US00PP35720P2

(12) United States Plant Patent
Clark

(10) Patent No.: US PP35,720 P2
(45) Date of Patent: Apr. 2, 2024

(54) ***COLEUS* PLANT NAMED 'UF22-146-3'**

(50) Latin Name: *Coleus scutellarioides*
Varietal Denomination: UF22-146-3

(71) Applicant: Florida Foundation Seed Producers, Inc., Marianna, FL (US)

(72) Inventor: David G. Clark, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 18/445,291

(22) Filed: Jun. 20, 2023

(51) Int. Cl.
*A01H 5/12* (2018.01)
*A01H 6/50* (2018.01)

(52) U.S. Cl.
USPC ..... Plt./469

(58) Field of Classification Search
USPC ..... Plt./469, 373
CPC ..... A01H 5/12; A01H 5/00; A01H 6/50
See application file for complete search history.

(56) References Cited

U.S. PATENT DOCUMENTS

PP14,790 P2 * 5/2004 Smith ..... A01H 6/50 Plt./373
PP31,425 P2 1/2020 Clark

* cited by examiner

*Primary Examiner* — June Hwu
(74) *Attorney, Agent, or Firm* — Koenig IP Works, PLLC; Katherine Koenig

(57) ABSTRACT

'UF22-146-3' is a new *Coleus* plant, selected for having a combination of desirable traits that make it well-suited for use as an annual plant in the summer landscape. 'UF22-146-3' was selected for its consistent and novel bright reddish brown to dark red foliage color and for its consistent compact and mounding habit and vigorous growth rate in the greenhouse and landscape. 'UF22-146-3' has large, lance-shaped leaves that are twice as long as they are wide. 'UF22-146-3' maintains its foliage colors and leaf patterns in both sun and shade until the end of the garden season. 'UF22-146-3' has a highly branched and spreading form, growing wider than it does tall.

3 Drawing Sheets

Genus and species: *Coleus scutellarioides*.
Cultivar denomination: 'UF22-146-3'.

CROSS-REFERENCE TO RELATED APPLICATIONS

N/A.

ACKNOWLEDGEMENT OF FEDERAL RESEARCH SUPPORT

N/A.

BACKGROUND OF THE NEW CULTIVAR

The invention relates to a new and distinct cultivar of *Coleus* plant named 'UF22-146-3'. The new cultivar 'UF22-146-3' originated from an open pollination conducted in May-November 2021 in Citra, Florida, between the female *Coleus* plant 'UF21-66-2' (unpatented) and an unknown male *Coleus* plant. A single seedling was chosen in May 2022 for further asexual propagation in Gainesville, Florida.

The new cultivar 'UF22-146-3' has been reproduced asexually for over 11 months through vegetative meristem tip cuttings and has been found to retain its distinctive characteristics through successive asexual propagations. 'UF22-146-3' was first propagated asexually by vegetative meristem tip cuttings in May 2022 in Gainesville, Florida, and has remained true-to-type since that time.

Plant Breeder's Rights for the new cultivar 'UF22-146-3' have not been applied for, and 'UF22-146-3' has not been made publicly available more than one year prior to the filing date of this application.

SUMMARY OF THE INVENTION

The new cultivar 'UF22-146-3' has not been observed under all possible environmental conditions. The phenotype of the new cultivar may vary with variations in environment and cultural practices such as temperature, light intensity, fertilization, irrigation, and application of plant growth regulators without any change in genotype.

The new cultivar 'UF22-146-3' was selected for its novel reddish brown to dark red foliage color and for its consistent, compact, and mounding habit in greenhouse-grown pots and landscape planting. 'UF22-146-3' is exceptional because it'maintains this novel color in both sun and shade. These characteristics allow the plant to have utility in mass outdoor ground plantings, or in containers as a specimen in small gardens.

The following are the most outstanding and distinguishing characteristics of 'UF22-146-3' when grown under normal horticultural practices in Gainesville, Florida: (1) 'UF22-146-3' has the combination of compact and mounding habit and spreading growth form, excellent heat tolerance, and consistent bright reddish brown to dark red foliage color that is significantly different than other *Coleus* plants; (2) it has superior stability in foliage color in both sun and shade conditions, and it has a vigorous growth habit with excellent lateral branching, making it suitable for propagators and producers; and (3) 'UF22-146-3' has been observed to have long-season performance in landscape trials in Gainesville, Florida.

When compared to the female parent 'UF21-66-2', 'UF22-146-3' has large, lance-shaped leaves that are twice as long as they are wide, whereas 'UF21-66-2' has large leaves that are equally as long as they are wide. Additionally, 'UF'22-146-3' has novel bright reddish brown to dark red colored leaves with yellow green accents and purplish red areas around the veins, whereas 'UF21-66-2' has deep crimson colored leaves and chartreuse margins and crimson netted patterning. 'UF22-146-3' has a vigorous compact and mounding growth habit and a spreading form that is well-branched, whereas 'UF21-66-2' is less vigorous, and more upright in habit with less lateral branching and a less spreading form.

DESCRIPTION OF THE FIGURES

This new *Coleus* cultivar 'UF22-146-3' is illustrated by the accompanying photographs, which show the plant's form and foliage. The colors shown are as true as can be reasonably obtained by conventional photographic procedures.

FIG. 2 shows the growth habit, form, and foliage of the new *Coleus* cultivar; and FIG. 3 shows a close-up view of the foliage of the new *Coleus* cultivar.

DETAILED BOTANICAL DESCRIPTION OF THE CULTIVAR

Figure 1:
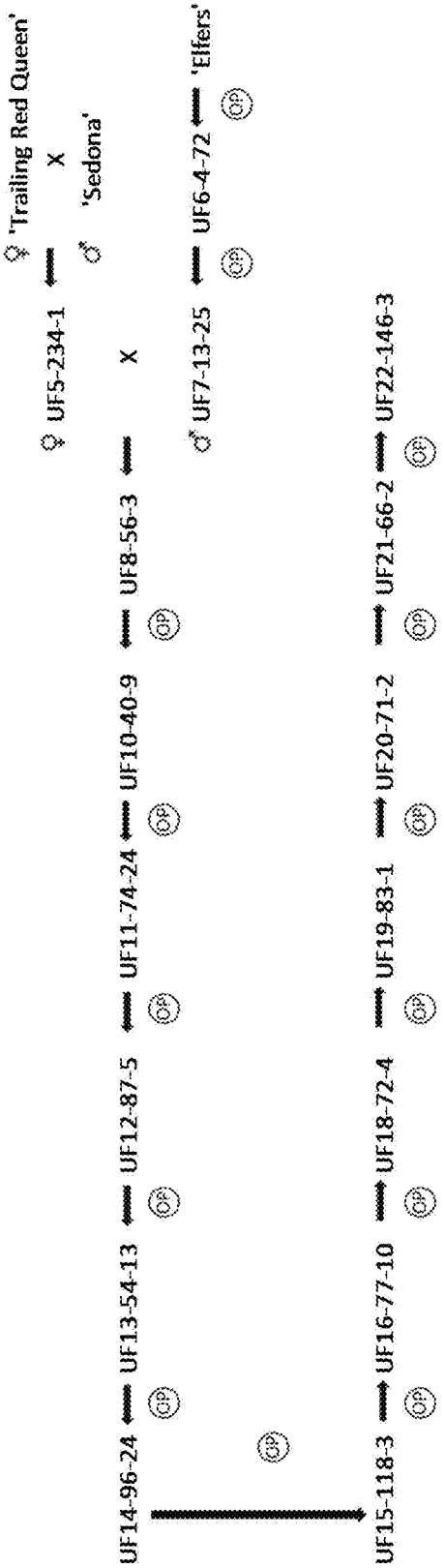
FIG. 1 shows the pedigree of the new *Coleus* cultivar 'UF22-146-3' as is shown and described herein, wherein the cultivar 'Sedona' has been patented as U.S. Plant Pat. No. 14,790 P2 (now expired)
Figure 2:
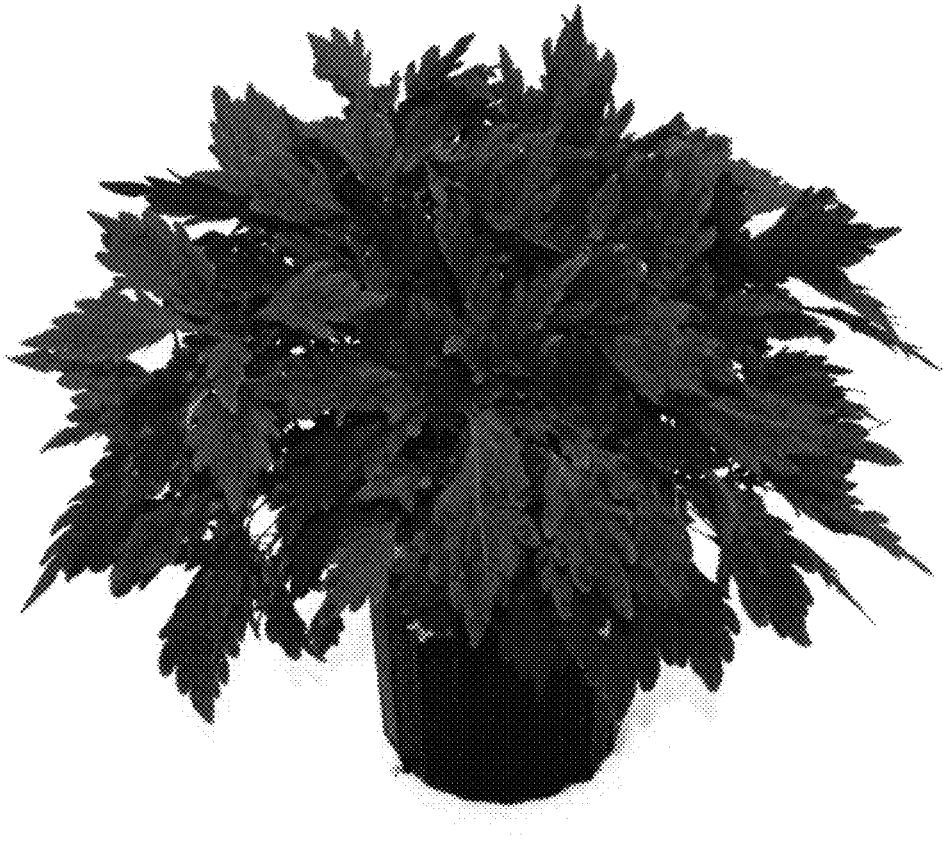
FIGS. 2 and 3 were taken from plants grown eleven weeks from unrooted cuttings in September-December 2022 in a glass-covered greenhouse in Gainesville, Florida.
Figure 3:
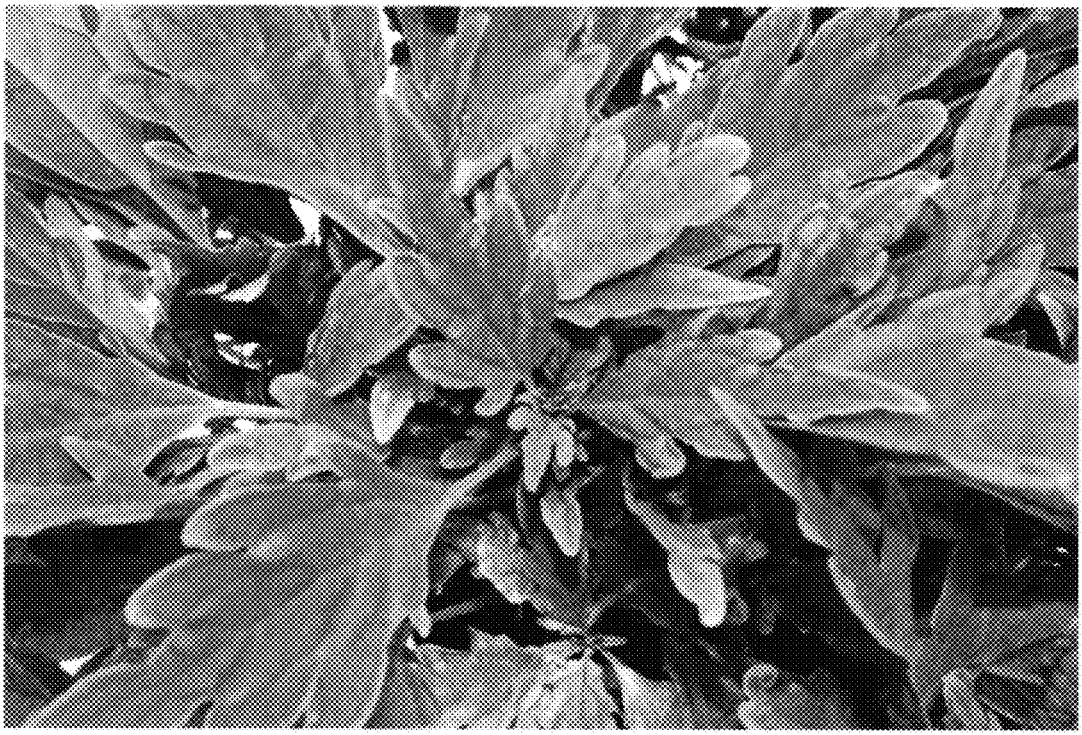

Foliage color was determined under full sun conditions in the middle of the day in a glass-covered greenhouse. Color references are to The R.H.S. Colour Chart of The Royal Horticultural Society of London (R.H.S.), 2007 5th Edition. *Coleus* leaves are rarely one solid color but encompass hues, shades and tints, and color patterns differ from one genotype to another due to varying levels of variegation. The following detailed description of 'UF22-146-3' was obtained using eleven-week-old plants grown from unrooted cuttings in September-December 2022 in a glass-covered greenhouse in Gainesville, Florida. The plants were propagated in mist for ten days after cuttings were stuck, pinched, then grown in one-gallon pots for approximately nine and a half additional weeks.

BOTANICAL DESCRIPTION

Botanical classification:
- *Family*.—Lamiaceae.
- *Botanical name*.—*Coleus scutellarioides*.
- *Common name*.—*Coleus*.
- *Cultivar name*.—'UF22-146-3'.

Parentage:
- *Female or seed parent*.—'UF21-66-2'.
- *Male or pollen parent*.—Unknown.

Plant description:
- *Form*.—Spreading.
- *Habit*.—Compact and mounding.
- *Height* (*from top of soil*).—18-22 cm.
- *Width* (*horizontal plant diameter*).—42-46 cm.

Propagation:
- *Type cuttings*.—Vegetative meristems having at least 1 node.
- *Time to initiate roots*.—3-4 days.
- *Time to produce a rooted cutting*.—7-10 days.
- *Root habit*.—Fibrous.
- *Root description*.—Callus forms in 2-3 days, roots initiate in 3-4 days and become a highly branched cutting in 7-10 days.

Branches:
- *Quantity per plant*.—Approximately 6.
- *Branch color*.—RHS N79A (purplish red).
- *Texture*.—Smooth.
- *Pubescence*.—Not present.
- *Stem description*.—Square-shaped stem.
- *Branch diameter*.—0.6-0.7 cm at the base of an 18-cm-long branch.
- *Branch length*.—18-20 cm.
- *Internode length*.—2 cm measured at mid-branch.
- *Anthocyanin*.—Not present.

Leaves:
- *Quantity of leaves per branch*.—22-24.
- *Arrangement*.—Opposite.
- *Fragrance*.—Not fragrant.
- *Shape*.—Lanceolate.
- *Length*.—8-9 cm.
- *Width*.—4-5 cm.
- *Apex*.—Broadly acute.
- *Base*.—Attenuate.
- *Margin*.—Lobed.
- *Leaf texture*.—Adaxial (top): Pulverulent. Abaxial (bottom): Smooth.
- *Venation color*.—Upper surface: RHS 59A (dark red). Lower surface: RHS N186D (purplish red).
- *Venation pattern* (*both upper and lower surfaces*).—Reticulate.
- *Color, immature. leaf*.—Upper surface: Major color: RHS 175A (reddish brown). Areas around veins: RHS 61C (purplish red). Accents: RHS 143C (yellow green). Lower surface: Major color: RHS N186D (dark purplish red).
- *Color, mature leaf*.—Upper surface: Major color: RHS 183A (dark red). Areas around veins: RHS 61B (purplish red). Accents: RHS 143C (yellow green). Lower surface: RHS N186C (greyish red).
- *Petiole length*.—6 cm.
- *Petiole diameter*.—0.1-0.2 cm.
- *Petiole color*.—RHS N77B (purplish red).
- *Petiole texture*.—Smooth, no pubescence.

Flowers and seeds: Flowers and seeds have not been observed during formal trials in Gainesville, Florida.

Fruit/seed set: Fruit/seed not observed.

Disease and insect resistance: Disease and insect resistance is typical of the species, thus no claims are made of any superior disease or insect resistance with this cultivar. The most common insect pests observed on this plant in Gainesville, Florida have been long-tailed or citrus mealybugs (*Pseudococcus* spp.), which occur on older stock plant material held in the greenhouse for over 3-4 months. Impatiens Necrotic Spot Virus (*Bunyaviridae*) has also been observed in plants confined in greenhouses with mixed crops (peppers) infected with Western flower thrips (*Frankliniella occidentalis*). The most common pathogen of this species in the U.S. is downy mildew (*Perononspora lamii*). This pathogen has been observed in stock materials grown closely together in cooler growing seasons.

COMPARISON WITH KNOWN CULTIVARS

When compared to the *Coleus* cultivar 'UF15-97-9' (U.S. Plant Pat. No. 31,425, commercial name Salsa Roja), the new *Coleus* cultivar 'UF22-146-3' has a leaf coloration that is bright reddish brown to dark red with areas around the veins colored purplish red on the upper surface of mature leaves and yellow green accents, whereas UF15-97-9 has a leaf coloration that is more purplish dark red with no coloration around the veins on the upper surface of mature leaves.

What is claimed is:

1. A new and distinct *Coleus scutellarioides* plant named 'UF22-146-3' as shown and described herein.

* * * * *